Jan. 10, 1939. K. CHRISTENSEN Plant Pat. 307
POINSETTIA
Filed March 23, 1938
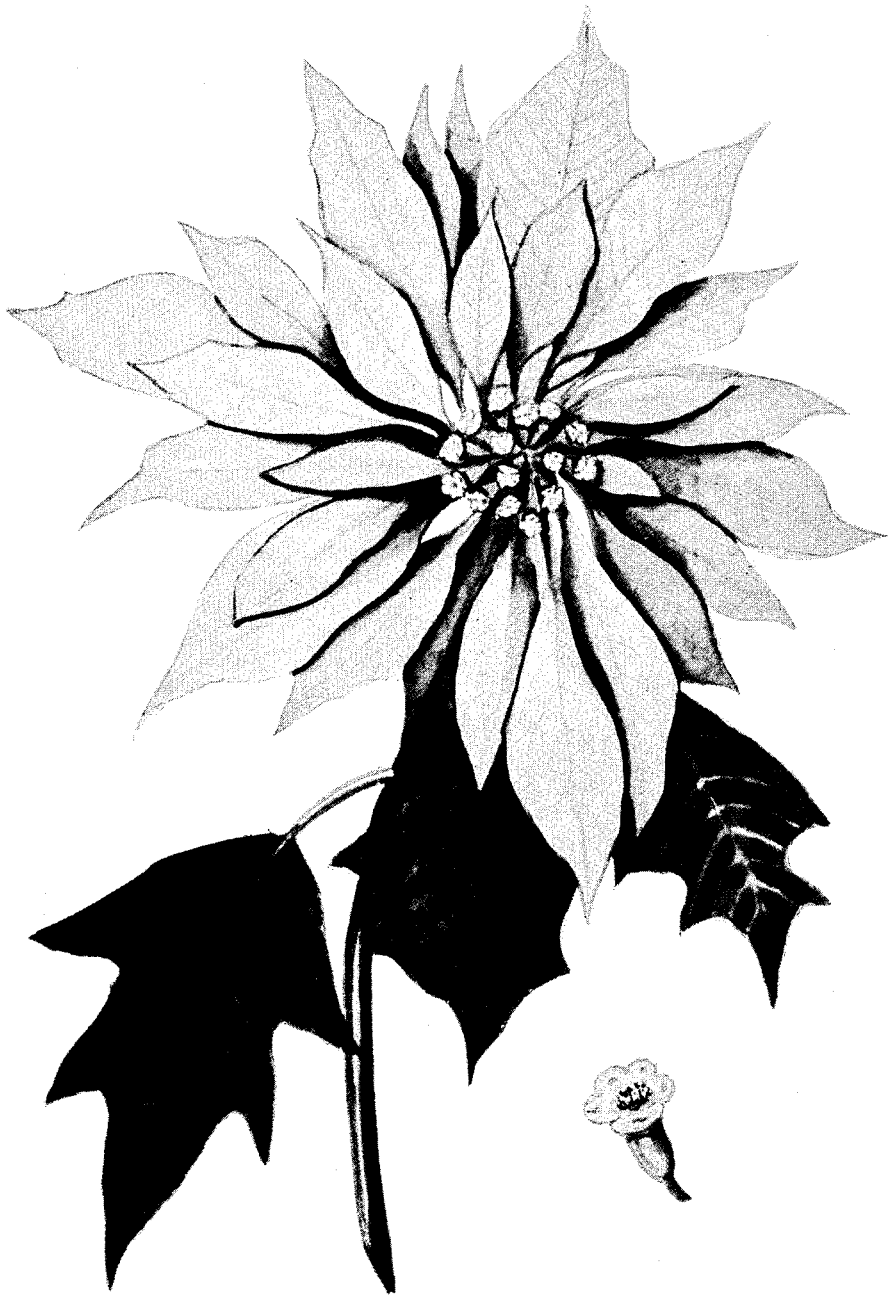
INVENTOR
Knud Christensen
By Orville M. Kile
Plant Patent Agent Patented Jan. 10, 1939

Plant Pat. 307

UNITED STATES PATENT OFFICE

307

POINSETTIA

Knud Christensen, Wood-Ridge, N. J., assignor to Madsen and Christensen, Inc., Wood-Ridge, N. J., a corporation of New Jersey Application March 23, 1938, Serial No. 197,703

1 Claim. (Cl. 47—60)

My present invention relates to improvements in poinsettias of the "oakleaf" type. This new variety is a sport of the variety Mrs. Paul Ecke and was discovered by me in the greenhouse of Madsen and Christensen in Wood-Ridge, New Jersey. The sport was discovered in a group of Mrs. Paul Ecke plants grown by us and stood out very distinct and entirely different from the surrounding plants. I have asexually reproduced this variety through four or five generations and its characteristics appear to be permanent.

One important novel characteristic of this new variety is the presence of five distinct nectar glands in each of the several compound flowers on a stem, rather than one gland as possessed by flowers of other known varieties. This feature gives a distinct decorative and star-like appearance.

Another very distinctive feature is the fact that there is practically no nectar in these nectar glands at any time. Since nectar from the glands spots the bracts when it comes into contact with them, this lack of nectar eliminates the spotting of the bracts, especially during shipping. This is a distinct advantage in preserving the beauty of the bracts. This feature, coupled with the fact that the bracts are less brittle than those of most varieties, makes this new variety an exceptionally good shipper.

The accompanying illustration portrays the front view of a specimen of this new poinsettia variety, in which a single stem is topped by a cluster or cyme of compound flowers, the whole being surrounded by a whorl of bracts. Below the bracts are shown several leaves at the stage when they are assuming the red color of maturity. Also at the lower right-hand corner is shown an enlarged view of one of the compound flowers of the cluster. The star-like formation of the five nectar glands of this variety is evident in the enlarged view.

Following is a more detailed description of this new variety.

*The plant*

The plant is a vigorous grower with heavy, sturdy stems. Because of this feature, staking and tying are usually unnecessary with this variety.

*The leaves*

The leaves are of the "oakleaf" type and are unusually large. Their color is between Spinach Green (Plate V, Ridgway's Color Standards and Nomenclature) and Dark Dull Yellow Green (Plate XXXII), when in their prime. However, when mature, the leaves nearest the blossoms change to shades of red, as do also the leaf peduncles.

*The flowers*

The flowers are compound, consisting of one pistillate flower surrounded by about a dozen staminate flowers, the whole being surrounded by a green, cup-like involucre having five lobes and five nectar glands. The nectar glands are somewhat more enlarged than in the usual poinsettia and since there are five instead of the usual one, the nectar glands are much more decorative in this variety than is usual. At the top of the involucre just inside the circle of nectar glands are many teeth of Scarlet-Red (Plate I), which give the compound flower the effect of having a Scarlet-Red center. The nectar glands surrounding the red center are Light Orange-Yellow (Plate III) and the cup of the involucre is Light Paris Green (Plate XVIII). There are fifteen or twenty of these compound flowers grouped together in a cluster or cyme at the top of the principal flower stem, and this cluster is surrounded by the bracts.

*The nectar glands*

Each compound flower has five distinct and complete nectar glands forming a complete circle at the top of the involucre, and presenting a star-like, decorative appearance—a characteristic which is distinct and different from any other known variety of poinsettia. However, these nectar glands have practically no nectar at any time and spotting and discoloration of bracts by the nectar is thus eliminated.

*The bracts*

Subtending and surrounding the cluster of compound flowers and forming a background therefor, are approximately twenty-five to thirty bracts of Scarlet Red to Spectrum Red (Plate I). These bracts are much darker than those of most varieties and their color is retained for an unusually long period. There are more bracts on this variety than on most other varieties, and these bracts are much less brittle than the bracts of other varieties. This latter feature makes them less easily broken in handling and is a particularly good point for shipping purposes.

*Comparisons*

Below I am giving specific comparisons with some of the leading poinsettia varieties, pointing out some of the principal differences.

*Comparison with Mrs. Paul Ecke.*—Bracts of this new variety are more numerous and not as brittle as those of the Mrs. Paul Ecke and are of a clearer and more brilliant color. This new variety is more vigorous in growth and has longer and larger leaves. The compound flowers of this variety have five large, distinct nectar glands which do not contain nectar, while the Mrs. Paul Ecke has only one nectar gland and it usually contains nectar.

*Comparison with Oak Leaf.*—Bracts of this new variety are more numerous, darker in color, and clearer than those of Oak Leaf. This new variety has larger and more abundant foliage than does Oak Leaf. The compound flowers of this new variety have five large nectar glands while Oak Leaf has only one nectar gland.

*Comparison with the Ruth Ecke.*—This new variety has bracts of a much darker color which retain their color a great deal longer than do those of the Ruth Ecke. This new variety has a heavier and much stronger stem than does the Ruth Ecke. This new variety has much larger leaves and many more bracts. This new variety has five complete, large nectar glands forming a star on each compound flower, while the Ruth Ecke has only one nectar gland for each compound flower.

Having thus disclosed my discovery, I claim;

The new and distinct variety of poinsettia plant, as herein shown and described, characterized particularly by its vigorous growth and strong, sturdy stems; its large and abundant foliage; the lack of brittleness, the brilliance and persistence of color, and the large number of its bracts; the presence of five large nectar glands forming a distinct star surrounding each compound flower; and the absence of nectar in the nectar glands.

KNUD CHRISTENSEN.